US010660797B2

(12) United States Patent
Hamer et al.

(10) Patent No.: US 10,660,797 B2
(45) Date of Patent: May 26, 2020

(54) PUSH-TO-FIT EARPLUG HAVING AN ARRAY OF CAVITIES

(71) Applicant: 3M INNOVATIVE PROPERTIES COMPANY, St. Paul, MN (US)

(72) Inventors: Jeffrey L. Hamer, Springville, IN (US); Kenneth F. Teeters, Zionsville, IN (US); Ravi Thomas, Avon, IN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 67 days.

(21) Appl. No.: 14/282,266

(22) Filed: May 20, 2014

(65) Prior Publication Data

US 2015/0335490 A1   Nov. 26, 2015

(51) Int. Cl.
*A61F 11/08*   (2006.01)

(52) U.S. Cl.
CPC .................. *A61F 11/08* (2013.01)

(58) Field of Classification Search
CPC ............. A61F 2011/085; A61F 11/008; A61F 11/06–12; H04R 1/10–1016; H04R 5/033–0335
USPC ................................................ 128/867, 868
See application file for complete search history.

(56) References Cited

U.S. PATENT DOCUMENTS

| | | |
|---|---|---|
| 3,638,370 A | 2/1972 | Miller |
| 4,314,553 A | 2/1982 | Westerdal |
| 4,452,021 A | 6/1984 | Anderson |
| 4,665,671 A | 5/1987 | Sarvis |
| D307,325 S | 4/1990 | Gardner, Jr. |
| D307,635 S | 5/1990 | Gardner, Jr. |
| D307,636 S | 5/1990 | Gardner, Jr. |
| D330,761 S | 11/1992 | Falco |
| D371,193 S | 6/1996 | Myers |
| 5,575,126 A | 11/1996 | Attaway |
| 5,799,658 A | 9/1998 | Falco |
| 5,816,625 A | 10/1998 | Clarke |
| D402,752 S | 12/1998 | Falco |
| 5,928,744 A * | 7/1999 | Heilmann ............... A61L 29/14 138/137 |

(Continued)

FOREIGN PATENT DOCUMENTS

| | | |
|---|---|---|
| CN | 2439507 | 7/2001 |
| CN | 301446540 | 1/2011 |

(Continued)

OTHER PUBLICATIONS

International Application PCT/US2015/030066 Search Report dated Aug. 10, 2015.

(Continued)

*Primary Examiner* — Alireza Nia
*Assistant Examiner* — Michelle J Lee
(74) *Attorney, Agent, or Firm* — Katherine M. Scholz; Christopher Karlen; Peter L. Olson

(57) ABSTRACT

The present description provides an earplug. One exemplary earplug described herein includes a stem and a sound attenuating body attached to the stem. The sound attenuating body includes a leading end, a base end, a tip region positioned rearward of the leading end, and a longitudinal axis extending between the leading end and the base end. An array of cavities is positioned within the tip region and spaced around the longitudinal axis and provides a collapsible volume.

20 Claims, 6 Drawing Sheets

(56) References Cited

U.S. PATENT DOCUMENTS

| | | | |
|---|---|---|---|
| 6,460,302 | B1 | 10/2002 | Neuhaus, III |
| D466,995 | S | 12/2002 | Knauer |
| D471,625 | S | 3/2003 | Falco |
| D478,658 | S | 8/2003 | Falco |
| D481,118 | S | 10/2003 | Doty |
| D492,765 | S | 7/2004 | Falco |
| D492,766 | S | 7/2004 | Falco |
| D493,219 | S | 7/2004 | Falco |
| D524,937 | S | 7/2006 | Doty |
| D524,938 | S | 7/2006 | Schreiber |
| D528,204 | S | 9/2006 | Doty |
| D536,089 | S | 1/2007 | Magidson |
| 7,264,081 | B2 | 9/2007 | Bruck |
| 7,314,047 | B2 | 1/2008 | Falco |
| 7,464,786 | B2 | 12/2008 | Falco |
| 7,537,011 | B2 | 5/2009 | Falco |
| D606,648 | S | 12/2009 | Benner |
| D636,484 | S | 4/2011 | Tiemens |
| 7,984,716 | B2 * | 7/2011 | Purcell .................. A61F 11/08 128/865 |
| 8,061,472 | B2 * | 11/2011 | Tiemens ................ A61F 11/08 181/135 |
| D651,302 | S | 12/2011 | Falco |
| D654,163 | S | 2/2012 | Tiemens |
| 8,113,207 | B2 | 2/2012 | Gehling |
| 8,679,607 | B2 | 3/2014 | Hamer |
| 2002/0066455 | A1 * | 6/2002 | Falco .................... A61F 11/00 128/864 |
| 2003/0196770 | A1 | 10/2003 | Wylie |
| 2004/0163882 | A1 * | 8/2004 | Fleming ................ A61F 11/10 181/135 |
| 2005/0274568 | A1 | 12/2005 | Falco |
| 2006/0162992 | A1 * | 7/2006 | Seville .................. A61F 11/08 181/135 |
| 2007/0149346 | A1 | 6/2007 | Onishi |
| 2008/0035281 | A1 | 2/2008 | Kirby |
| 2010/0307514 | A1 | 12/2010 | Berg |
| 2013/0188819 | A1 | 7/2013 | Young-Mun |
| 2014/0014121 | A1 | 1/2014 | Endle |
| 2014/0015157 | A1 | 1/2014 | Endle |
| 2014/0017492 | A1 | 1/2014 | Hamer |
| 2015/0335489 | A1 | 11/2015 | Hamer |

FOREIGN PATENT DOCUMENTS

| | | |
|---|---|---|
| CN | 201851555 | 6/2011 |
| EM | 000068796-0001 | 11/2003 |
| EM | 000117510-0002 | 3/2004 |
| EM | 000252424-0001 | 2/2005 |
| EM | 000252424-0002 | 2/2005 |
| EM | 000252424-0003 | 2/2005 |
| EM | 000568217-0001 | 9/2006 |
| EM | 001097497-0002 | 3/2009 |
| EM | 001097497-0003 | 3/2009 |
| EM | 001097505-0002 | 4/2009 |
| EM | 001211056-0001 | 7/2010 |
| EM | 001211056-0002 | 7/2010 |
| EM | 001211056-0003 | 7/2010 |
| EM | 002291005-0001 | 11/2013 |
| GB | 1050275 | 11/1988 |
| GB | 2043262 | 3/1995 |
| GB | 2045159 | 3/1995 |
| GB | 4014253 | 2/2010 |
| JP | 44-031107 | 12/1969 |
| JP | H05164199 | 6/1993 |
| JP | 2007-062060 | 3/2007 |
| JP | 2007-107689 | 4/2007 |
| JP | 2010-059630 | 3/2010 |
| JP | D1405724 | 12/2010 |
| KR | 2009-0113923 | 11/2009 |
| SU | 822821 | 4/1981 |

OTHER PUBLICATIONS

U.S. Appl. No. 14/282,252 to Hamer filed May 20, 2014, entitled *Push-to-Fit Earplug Having Geometric Flange Features*.

U.S. Appl. No. 61/925,770 to Teeters et al. filed Jan. 10, 2014, entitled *Molded Foam Push-to-Fit Earplug, Method, and Device*.

* cited by examiner

PUSH-TO-FIT EARPLUG HAVING AN ARRAY OF CAVITIES

TECHNICAL FIELD

This disclosure relates to a hearing protection device, in particular a push-to-fit earplug having a tip region and an array of cavities positioned in the tip region and spaced around the longitudinal axis that provide a collapsible volume.

BACKGROUND

The use of hearing protective and noise attenuating devices are well known, and various types of devices have been considered. Such devices include earplugs and semi-aural devices partially or completely constructed of foam or rubber materials that are inserted into, or placed over, the ear canal of a user to physically obstruct the passage of sound waves into the inner ear.

Compressible or "roll-down" type earplugs generally comprise a compressible, resilient body portion and may be made of suitable slow recovery foam materials. The earplug may be inserted into the ear canal of a user by first rolling it between fingers to compress the body portion, then pushing the body portion into the ear canal, and subsequently allowing the body portion to expand to fill the ear canal.

Push-to-fit type earplugs have also been considered, and may include a compressible attenuating portion and a stiff portion that extends from the attenuating portion. To insert a push-to-fit type earplug, the user grasps the stiff portion and pushes the attenuating portion into the ear canal with an appropriate level of force. The attenuating portion compresses as it is accommodated in the ear canal. Push-to-fit earplugs may allow the earplug to be quickly and easily inserted in an ear canal, and may promote hygiene by minimizing contact with the attenuating portion of the earplug prior to insertion.

SUMMARY

The present description relates to an earplug, such as a push-to-fit earplug. In an exemplary embodiment, an earplug includes a stem and a sound attenuating body attached to the stem. The sound attenuating body includes a leading end, a base end, a tip region positioned rearward of the leading end, and a longitudinal axis extending between the leading end and the base end. An array of cavities is positioned within the tip region and spaced around the longitudinal axis, and the array of cavities provides a collapsible volume. In an exemplary embodiment, the tip region comprises a cavity area (Ac), a material area (Am) and an area aspect ratio (Ac/Am) at a plane intersecting the array of cavities transverse to the longitudinal axis, and $0.10 < (Ac/Am) < 0.35$.

The present description further provides, in another exemplary embodiment, an earplug including a stem and a sound attenuating body attached to the stem. The sound attenuating body includes a leading end, a base end, a tip region positioned rearward of the leading end, and a flange extending at least partially over the stem and comprising an exterior flange surface and an interior flange surface having a plurality of one or both of protrusions or recesses and a longitudinal axis extending between the leading end and the base end. The earplug further includes an array of cavities positioned within the tip region and spaced around the longitudinal axis, the array of cavities including a collapsible volume; and a flange cavity including a continuous volume around a perimeter of the stem between the interior flange surface and the stem. The tip region comprises a cavity area (Ac), a material area (Am) and an area aspect ratio (Ac/Am) at a plane intersecting the array of cavities transverse to the longitudinal axis, and $0.10 < (Ac/Am) < 0.35$.

The above summary is not intended to describe each disclosed embodiment or every implementation. The Figures and the Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

An earplug that provides hearing protection for a user is provided herein. An earplug according to the present disclosure includes a stem and a sound attenuating body having a flange. When inserted into the ear canal of a user, the sound attenuating body is able to compress and at least partially collapse into a collapsible volume provided by an array of cavities in a tip region. The array of cavities provide additional volume into which a portion of the sound attenuating body can collapse, reducing an insertion force required to position the earplug in an ear canal and reducing an equilibrium force exerted by the earplug and acting on a user's ear canal when the earplug is positioned for use. An earplug having an array of cavities in a tip region as described herein facilitates an earplug that is easy to insert and comfortable to wear.

Figure 1:
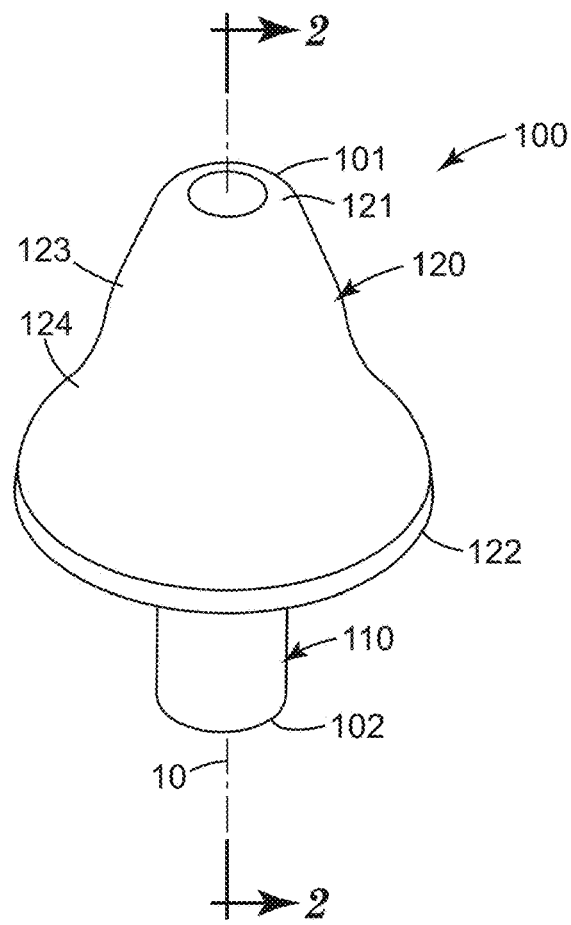
FIG. 1 is a front perspective view of an exemplary earplug according to the present description.
Figure 2:
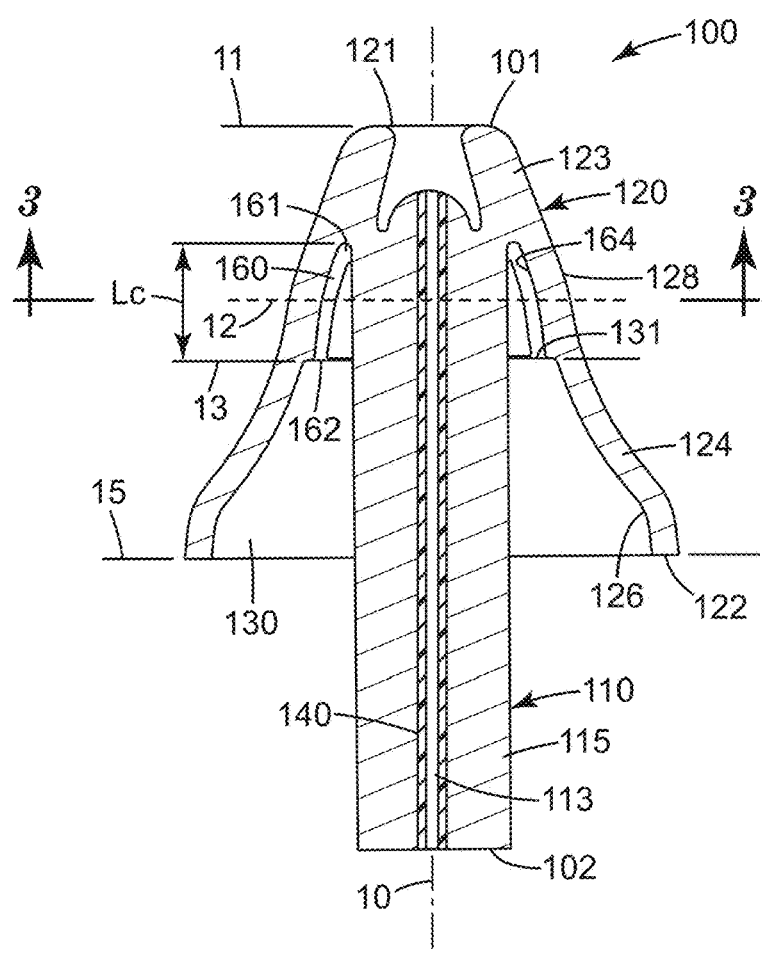
FIG. 2 is a cross-sectional view of an exemplary earplug according to the present description.
Figure 3:
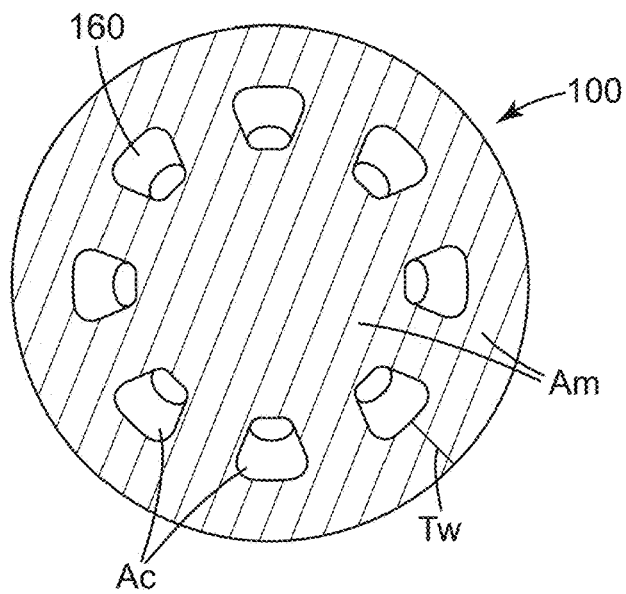
FIG. 3 is a cross-sectional view of an exemplary earplug according to the present description taken across line 3-3 of FIG. 2.

FIGS. 1 through 3 show an exemplary push-to-fit earplug 100 including a stem 110 and sound attenuating body 120 and having first and second ends 101 and 102. Sound attenuating body 120 is configured for at least partial insertion into the ear canal of a user to attenuate the passage of sound into the ear canal. During insertion of earplug 100, stem 110 may serve as a handle which may be gripped by a user. Earplug 100, and specifically sound attenuating body 120, is brought proximate to the user's ear and at least partially inserted into the ear canal. Sound attenuating body 120 compresses and/or collapses as it is positioned, and stem 110 provides sufficient stiffness to facilitate insertion. In use, sound attenuating body 120 is positioned substantially within an ear canal to block the passage of sound and stem 110 extends outwardly from the ear canal to provide a handle to remove the earplug.

In an exemplary embodiment, sound attenuating body 120 includes a leading end 121, a base end 122, a tip region 123 and a flange 124 extending at least partially over stem 110. Tip region 123 is located rearwardly of leading end 121 and flange 124 is located between tip region 123 and base end 122. In some exemplary embodiments, sound attenuating body 120 defines a flange cavity 130 between stem 110 and sound attenuating body 120. In an exemplary embodiment, flange cavity 130 is defined at least in part by stem 110, sound attenuating body 120, and a flange cavity bottom 131. Flange cavity bottom 131 may be formed by a portion of tip region 123, where stem 110 and sound attenuating body 120 intersect, for example.

Certain features of an earplug according to the present description may be understood in view of various reference planes defined relative to earplug 100 and shown in FIG. 2. A longitudinal axis 10 extends between leading end 121 and base end 122 of sound attenuating body 120. A leading end plane 11 passes across an outermost tip of leading end 121, and/or first end 101, of earplug 100 transverse to the longitudinal axis, and a flange end plane 15 intersects earplug 100 transverse to longitudinal axis 10 at base end 122 of flange 124. In various exemplary embodiments, a cavity plane 13 intersects earplug 100 at a forward-most portion of flange cavity 130.

In an exemplary embodiment, flange 124 is not attached to stem 110 within flange cavity 130, or between cavity plane 13 and base end 122, and only attaches to stem at and/or above cavity plane 13. Flange 124 may be defined as that portion of sound attenuating body 120 that is located below the cavity plane 13. Because flange 124 is connected to a remainder of sound attenuating body 120 and/or stem 110 only near one end, flange cavity 130 includes a continuous volume around stem 110. That is, in an exemplary embodiment, an interior flange surface 126 of flange 124 does not contact stem 110 when in a neutral, uncompressed configuration such as when not positioned in an ear canal. In an exemplary embodiment, the flange cavity includes a continuous uninterrupted volume around a perimeter of at least a portion of stem 110. Flange 124 may deflect inwardly as earplug 100 is advanced into an ear canal and/or is positioned therein, and in some embodiments interior flange surface 126 may at least partially contact stem 110. In various exemplary embodiments, deflection and/or compression of flange 124 may improve insertion, comfort, and sound attenuation, and may be controlled by the materials, geometry, and configuration of earplug 100.

Earplug 100 includes an array of cavities 160 positioned within tip region 123 and spaced around the longitudinal axis 10. Cavities 160 provide a collapsible volume that at least a portion of sound attenuating body 120 may collapse into as earplug 100 is advanced into an ear canal of a user. Collapsible volume provided by cavities 160 provides an earplug 100 that may be comfortably inserted and worn by a user while providing a desired level of sound attenuation. The geometry and configuration of cavities 160 may be selected as described herein to provide a desire balance of fit for a range of users having varied ear canal shapes and sizes.

Cavities 160 may be positioned around longitudinal axis 10 and extend within tip region 123 of earplug 100. In an exemplary embodiment, earplug 100 includes a flange cavity 130 between stem 110 and sound attenuating body 120 and having a flange cavity bottom 131. Cavities 160 are positioned between flange cavity bottom 131 and leading end 121 of sound attenuating body 120 (e.g. between cavity plane 13 and leading end plane 11).

In an exemplary embodiment, the array of cavities 160 extend between first and second cavity ends 161 and 162 and have a generally elongate shape. First cavity end 161 may be the forward-most portion of array of cavities 160 nearest to leading end 121 and second cavity end 162 may be the rearward-most portion of array of cavities 160 furthest from leading end 121. In various exemplary embodiments, cavities 160 have a length (Lc) between first and second cavity ends 161 and 162 between about 1.0 mm and 6.0 mm, 2.0 mm and 5.0 mm, or of about 4.0 mm.

In an exemplary embodiment, first cavity end 161 is between 3.5 mm and 8.0 mm, 4.5 mm and 7.3 mm, or about 5.5 mm from leading end 121 of sound attenuating body 120. Such a distance allows for sufficient stiffness such that leading end 121 may be readily inserted into a user's ear. Second cavity end 162 is at least partially open and in communication with flange cavity 130, and second cavity end 162 may be located proximate cavity plane 13.

Array of cavities 160 are sized to provide a desirable collapsible space to reduce a force required to compress sound attenuating body 120 when earplug 100 is at least partially inserted into an ear canal of a user. In various exemplary embodiments, such as shown in FIG. 3, tip region 123 of sound attenuating body 120 may be characterized as having a cavity area (Ac) and a material area (Am) at a plane intersecting array of cavities 160 transverse to the longitudinal axis, such as plane 12. Cavity area (Ac) is an area of open space within each cavity 160, and material area (Am) is the remaining area of tip region 123 of earplug 100 including material, such as foam material and cells that may be present in the material. In various exemplary embodiments, cavity area (Ac) may be between 4 $mm^2$ and 36 $mm^2$, 6 $mm^2$ and 24 $mm^2$, or about 12 $mm^2$, and material area (Am) may be about 45 $mm^2$ to 65 $mm^2$, 50 $mm^2$ to 60 $mm^2$, or about 55 $mm^2$.

In an exemplary embodiment, array of cavities 160 exhibits an area aspect ratio (Ac/Am) of cavity area (Ac) to material area (Am). In various exemplary embodiments, (Ac/Am) is between 0.04 and 0.35, 0.10 and 0.30, or about 0.22, and in some exemplary embodiments may exhibit an area aspect ratio (Ac/Am) within such ranges when plane 12 passes through array of cavities at a distance between 4.5 mm and 8.0 mm from leading end 121. A maximum area aspect ratio (Ac/Am) exists at a plane passing through array of cavities transverse to longitudinal axis 10 at a location in which (Ac/Am) is greatest. In an exemplary embodiment, maximum area aspect ratio (Ac/Am) at plane 12 intersecting array of cavities 160 at a distance between 7.0 mm and 10.0 mm is between 0.10 and 0.35, 0.16 and 0.28, or about 0.22. In various exemplary embodiments, maximum area aspect ratio (Ac/Am) occurs at second end 162, for example at cavity plane 13, and the cavities taper such that (Ac/Am) decreases at locations closer to first end 161 of array of cavities 160.

Array of cavities 160 result in a reduced wall thickness (Tw) between an interior surface 164 of cavity 160 and an exterior surface 128 of tip region 123. Reduced wall thickness (Tw) may be selected to provide a required level of durability such that earplug does not readily tear or break while also not being so thick so as to unduly increase equilibrium force. In various exemplary embodiments, reduced wall thickness is between 1.0 mm and 2.5 mm, 1.1 mm and 1.7 mm, or about 1.25 mm.

An exemplary earplug 100 having dimensions and cavity area (Ac) within the above ranges provides additional collapsible space for material of tip region 123 to compress into as tip region 123 is positioned and resident in an ear canal of a user. In an exemplary embodiment, such ranges may result in a desired equilibrium force exerted by tip region 123 when residing in an ear canal of a user. Equilibrium force is a force exerted by earplug 100 to return to an original, uncompressed state and is related to a force exerted on a user's ear canal when earplug 100 is positioned for use. Accordingly, array of cavities 160 having a cavity area (Ac) within such ranges provides a reduced equilibrium force to maximize comfort while ensuring sufficient force that earplug 100 may be maintained in position in a user's ear canal. In various exemplary embodiments, array of cavities 160 can reduce equilibrium force between 5% and 50%, 10% and 40%, or about 25% as compared to an earplug having the same material and geometry but not having an array of cavities.

Figure 4A:
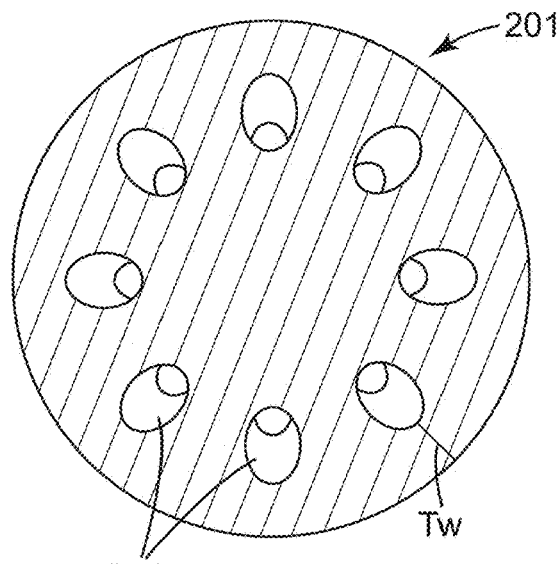
FIGS. 4a and 4b are cross-sectional views of variations of the exemplary earplug taken across line 3-3 of FIG. 2 and according to the present description showing an array of cavities having various cavity shapes.
Figure 4B:
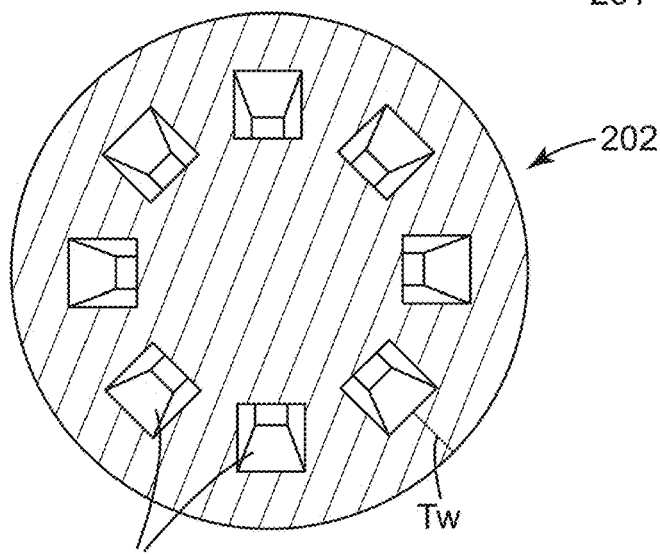

Array of cavities 160 may include any suitable number and shape of cavities. In various exemplary embodiments, array of cavities 160 includes between 4 and 24, 6 and 18, or about 8 cavities 160. Cavities 160 may have any desired cross-sectional shape and may vary along a length of the cavities, for example between first and second cavity ends 161, 162. In an exemplary embodiment of FIGS. 1 through 3, cavities 160 have a generally trapezoidal shape, and is only one example of many suitable shapes for cavities as described herein. Other exemplary shapes, include, but are not limited to, the shapes of FIGS. 4a and 4b. FIGS. 4a and 4b show earplugs 201 and 202 having an array of cavities 261, 262 that exhibit oval, or otherwise arcuate, and quadrilateral cavities.

Figure 5:
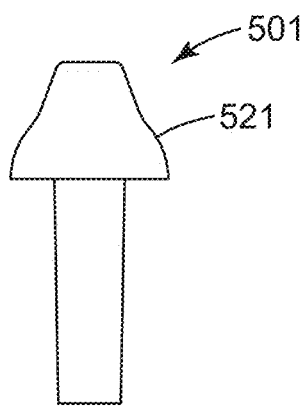
FIG. 5 is a side view of an exemplary earplug according to the present description showing an exemplary sound attenuating body profile.

An exemplary earplug as described herein may have any suitable shape or profile to provide a desired fit or that may be suitable for a particular application. The specific shape of sound attenuating body 120 of the exemplary embodiment depicted in FIGS. 1 through 3 is only one example of a potentially suitable shape for an earplug as described herein. Examples of one of the myriad of alternative shapes that could be used for earplugs as described herein is depicted in FIG. 5 showing exemplary earplug 501 having sound attenuating body 521.

In some exemplary embodiments, a channel 113 extends through earplug 100 between first and second ends 101, 102. Earplugs as described herein that include channels passing through the earplug may be manufactured such that components of a receiver or of a communication system may be attached to the earplug. Alternatively or in addition, channel 113 may accommodate one or more filters or other passive hearing elements to provide an attenuation curve having a desired shape. For example, filters positioned in channel 113 may cause nonlinear attenuation of high level impulses produced by explosions, gunfire, or the like. Channels provided in one or more embodiments of earplugs as described herein may also provide a recess that a cord may be attached to, such that first and second earplugs may be joined, or that ends of a headband may be attached to in a semi-aural hearing protector.

Earplugs as described herein may be manufactured in any suitable manner. In an exemplary embodiment, earplug 100 includes a core 140 that provides a substrate onto which an outer layer of material may be provided and, in one or more embodiments, may facilitate insertion into an ear canal of a user. Core 140 is made of a first material that exhibits greater rigidity or stiffness than a second material that forms sound attenuating body 120, yet that is soft enough to be comfortable and safe for a user. In an exemplary embodiment, the first material of core 140 is different than the second material used to form sound attenuating body 120 and/or an outer layer 115 of stem 110. In other exemplary embodiments, the first and second materials are similar or the same chemically, but may be formed or provided in a manner that results in different stiffnesses between the first material and the second material, for example due to differing density, cell structure, hardness, etc.

Including a core 140 in the stem 110 that is stiffer than the material of sound attenuating body 120 and/or outer layer 115 of the stem 110 may, in one or more exemplary embodiments, provide a stem 110 having sufficient rigidity so that the earplugs described herein may be positioned for use at least partially in the ear of a user by pushing sound attenuating body 120 into the ear canal with an appropriate force. That is, a sufficiently stiff stem 110 may be provided by a core 140 and an outer layer 115 of the material used to form the sound attenuating body 120 so that earplug 100 may be positioned for use at least partially in the ear of a user without the need to first compress or "roll down" sound attenuating body 120. Direct insertion without the need to first compress or "roll down" sound attenuating body 120 may, for example, promote hygiene by limiting contact with sound attenuating body 120 prior to placement in the ear. In one or more embodiments, core 140 may also exhibit an appropriate level of flexibility such that it may slightly deform to follow the contours of the ear canal when positioned for use.

Core 140 may, in one or more exemplary embodiments, be made from one or more materials that can suitably bond to, and are otherwise compatible with, the material used to form the sound attenuating body 120 and/or, when present, outer layer 115 of stem 110. In one or more embodiments, core 140 may be made from a blend of polypropylene and styrene-ethylene-butylene-styrene (SEBS), such as TUF-PRENE available from S&E Specialty Polymers, LLC. of Lunenburg, Mass. or PPC1TF2 available from Washington Penn Plastic Co., Inc. of Washington, Pa. Other potentially suitable materials include SANTOPRENE 101-90, available from Exxon Mobile Corporation, and other materials exhibiting appropriate stiffness such that sound attenuating body 120 of earplug 100 may be easily inserted into the ear canal of a user.

A second material used to form sound attenuating body and, in one or more embodiments, an outer layer of a stem of an earplug as described herein, may be soft and pliable foam, rubber, polymer, or other suitable material that may be comfortably positioned in an ear canal of a user. In one or more exemplary embodiments, the second material is an SEBS, such as MONPRENE MP1900 available from Teknor Apex of Pawtucket, R.I., or a blend of high and low molecular weight Kraton SEBS resins resulting in a hardness of 32 Shore A, available from Kraton Polymers LLC, of Houston, Tex., that provides a cellular foam. Other suitable materials include plasticized polyvinyl chloride, ethylene propylene diene monomer (EPDM) rubber, styrene butadiene rubber (SBR), butyl rubber, natural rubbers, other thermoplastics, thermoset polymers, and other suitable materials as known in the art that can be formulated to exhibit an appropriate hardness range.

In one or more embodiments, the materials used to construct a core and sound attenuating body may be selected such that the primary source of bonding between the core and material used for the sound attenuating body (directly or indirectly) is thermal bonding. In one or more embodiments, an additional adhesive is not required to bond the core to the sound attenuating body and, as a result, an adhesive is not present between the core and the sound attenuating body. Although the sound attenuating body of an earplug as described herein may be described as being constructed of a second material, in one or more embodiments a sound attenuating body may be constructed of multiple layers of the same or different materials (which may be, e.g., arranged concentrically). For example, a first layer may be used to provide desired characteristics for contacting an ear canal of a user and a second layer may be used to facilitate a robust bond with the core, while one or more additional layers may be used to provide other desired characteristics.

Materials used in the sound attenuating body of earplugs as described herein may be selected to control the friability of the outer surface of the sound attenuating bodies such that it may not easily be broken or disintegrate during use. The friability of an earplug may be controlled in part by selecting a material having an appropriate molecular weight, with higher molecular weight generally resulting in a less friable earplug. In an exemplary embodiment, sound attenuating body 120 includes an SEBS having a molecular weight between 100,000 Daltons and 200,000 Daltons, as measured by gel permeation chromatography analysis as known in the art, such as according to ASTM D6474-99.

The density of outer layer of second material used in the sound attenuating bodies as used in earplugs as described herein can, in one or more embodiments, be controlled during manufacturing to provide a specified density as desired for a particular application. The second material may, in one or more embodiments, exhibit a density that varies by thickness, for example, such that the second material used in the sound attenuating body has an integral outer skin that has a higher density than the second material located closer to the core. Such a skin may be present on one or both of sound attenuating body and the stem (in embodiments in which the stem includes, for example, a layer of the second material used in the sound attenuating body). Alternatively, the second material used to construct the sound attenuating body and/or an outer layer of the stem may have a substantially uniform density. In various exemplary embodiments, the average density of the sound attenuating portion, comprising a foamed SEBS for example, is between 100 kg/m$^3$ and 180 kg/m$^3$, or 110 kg/m$^3$ and 160 kg/m$^3$, or may be about 125 kg/m$^3$.

U.S. patent application Ser. No. 13/547,189, titled Method of Making an Earplug, addresses a method of making personal protective equipment such as a push-to-fit earplug, U.S. patent application Ser. No. 13/547,177, titled Push-In Earplug, addresses the structure and configuration of a push-to-fit earplug, and U.S. patent application Ser. No. 13/547,294, titled Foamable Article, addresses an article for forming a device or component, and are incorporated herein by reference.

In some exemplary embodiments, earplug 100 may be formed from a single material or first and second materials that are similar or the same chemically, but formed or provided in a manner that results in different stiffnesses between the first material and the second material, for example due to differing density, cell structure, hardness, etc. For example, a stem and sound attenuating body having differing properties may be formed by controlling venting in a molding process, and a core 140 may not be included. U.S. Application Ser. No. 61/925,770, Molded Foam Push-To-Fit Earplug, Method, and Devices, incorporated herein by reference, describes techniques for making an earplug having a sound attenuating body and stiffer stem formed from the same or similar materials.

In various exemplary embodiments, stem 110 and sound attenuating body 120 may be formed separately and subsequently joined together. For example, sound attenuating body 120 may be formed from any suitable soft and pliable foam, rubber, polymer, or other suitable material, as described above, and stem 110 may be formed of a more rigid material. Stem 110 and sound attenuating body 120 are then permanently or removably joined, for example by an adhesive, friction, or other engagement.

Figure 6A:
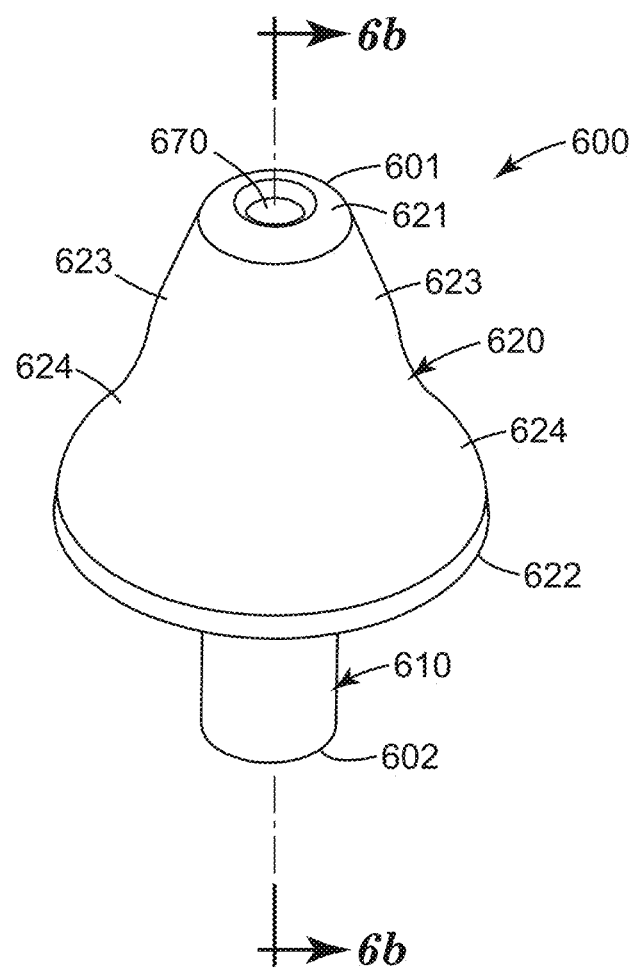
FIG. 6a is a front perspective view of an exemplary earplug according to the present description having a sound attenuating body including a tip cavity and geometric features on an interior flange surface.
Figure 6B:
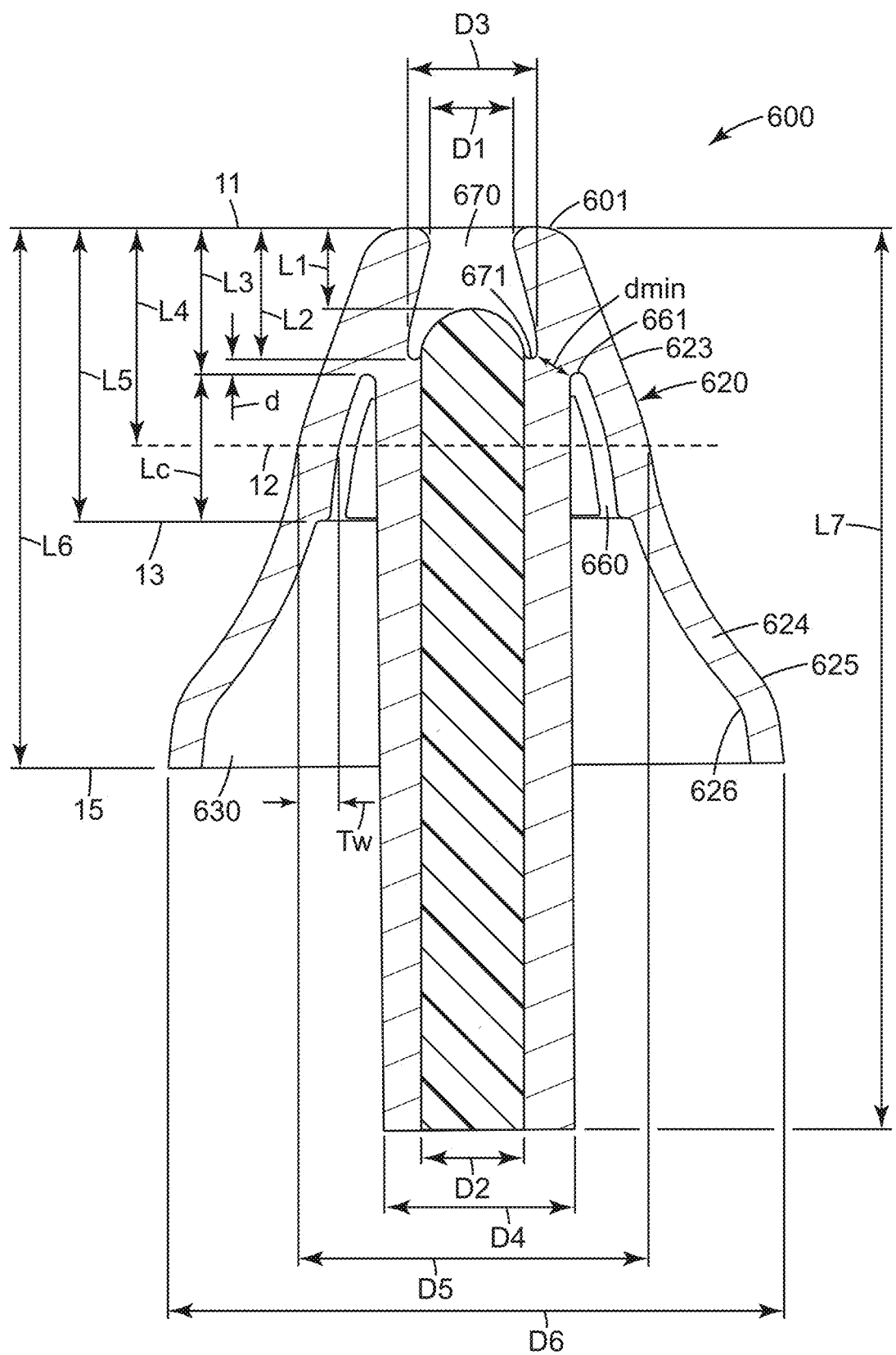
FIG. 6b is a cross-sectional view of an exemplary earplug according to the present description including a tip cavity and geometric features on an interior flange surface.
Figure 6C:
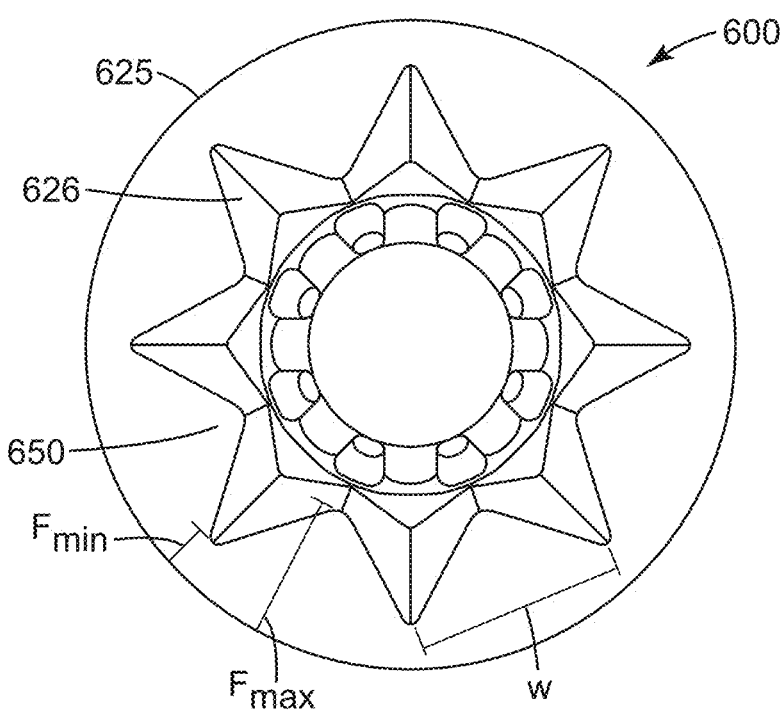
FIG. 6c is a bottom view of an exemplary earplug according to the present description including a tip cavity and geometric features on an interior flange surface.

An earplug as described herein may include various other geometric features to enhance comfort or provide improved attenuation. FIGS. 6a through 6c show an exemplary push-to-fit earplug 600 including a stem 610 and sound attenuating body 620 and having first and second ends 601 and 602. Sound attenuating body 620 includes a leading end 621, a base end 622, a tip region 623 and a flange 624. Tip region 623 is located rearwardly of leading end 621 and flange 624 is located between tip region 623 and base end 622. Similar to exemplary earplug 100, sound attenuating body 620 includes an array of cavities 660 positioned within tip region 623 and spaced around the longitudinal axis 10. Cavities 660 provide a collapsible volume that at least a portion of sound attenuating body 620 may collapse into as earplug 100 is advanced into an ear canal of a user.

Exemplary earplug 600 includes a tip cavity 670 that extends from first end 601 of earplug 600 towards a bottom 671 located nearer second end 602 of earplug 600. Tip cavity 670 includes an opening at first end 601 of earplug 600. Tip cavity 670 may, in one or more exemplary embodiments, provide a volume into which the surrounding material of sound attenuating body 620, and particularly tip region 621, can collapse as earplug 600 is advanced into an earcanal and/or is resident therein. U.S. application Ser. No. 13/768, 214, Earplug with Tip Cavity and Methods of Manufacturing the Same address earplugs having a tip cavity, and is incorporated herein by reference.

In an exemplary embodiment, bottom 671 of tip cavity 670 may be spaced from a first end 661 of cavities 660. For example, bottom 671 of tip cavity 670 may be spaced a distance (d min) from a portion of cavities 660, such as first end 661 of cavities 660. In various exemplary embodiments, a minimum distance (d min) between tip cavity 670 and one or more cavities 660 is between at least 0.3 mm and 3.0 mm, 1 mm and 2.5 mm, or of about 1.5 mm. A minimum distance (d min) within such ranges results in a sufficient stiffness such that a leading end 621 of earplug 600 may be inserted in a user's ear, and improves strength and durability to withstand repeated uses.

In an exemplary embodiment, earplug 600 further includes various geometric features 650 of an interior flange surface 626 such that a distance between exterior and interior flange surface 625, 626 varies and flange 624 exhibits different thickness around a perimeter of the flange at a plane intersecting the flange transverse to the longitudinal axis. For example, flange 624 may be characterized by a minimum flange thickness (F min) and a maximum flange thickness (F max) between exterior flange surface 625 and interior flange surface 626. In an exemplary embodiment, flange 624 includes a plurality of geometric features in the form of splines 650 spaced about flange 624 and extending from base end 622 of flange 624 at least partially towards bottom 631 of flange cavity 630. Splines 650 exhibit a width (w) between two adjacent locations of a minimum flange thickness (F min). Geometric features, such as protrusions, recess, or splines 650, affect collapse and/or compression of flange 624 such that undesirable creasing or buckling of flange 624 is minimized. An earplug having such geometric flange features facilitates an earplug that is comfortable to wear and minimizes undue noise leakage into an ear canal by limiting creasing or buckling of the flange. U.S. Pat. App. Pub. No. 2015/0335489, Push-To-Fit Earplug Having Geometric Flange Features addresses earplugs having a plurality of inwardly projecting geometric features and is herein incorporated by reference.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures. Any patent literature cited herein is hereby incorporated herein by reference in its entirety to the extent that it does not conflict with the description presented herein.

Any feature or characteristic described with respect to any of the above embodiments can be incorporated individually or in combination with any other feature or characteristic, and are presented in the above order and combinations for clarity only. That is, the present disclosure contemplates all possible combinations and arrangements of various features of each of the exemplary embodiments and components describe herein, and each component may be combined or used in conjunction with any other component as may be desired for a particular application.

EXAMPLES

The characteristics, operation, and advantages of the present invention may be further understood with regard to the following detailed non-limiting examples. These examples are offered to further illustrate the various specific and preferred embodiments and techniques. It should be understood, however that many variations and modifications may be made while remaining within the scope of the present invention.

Procedure 1: Equilibrium Force Test

Equilibrium force is a rebound force exerted by an earplug when compressed and represents a force exerted by an earplug when positioned in a user's ear canal. Equilibrium force may provide an indication of a relative level of comfort of an earplug.

Equilibrium force was obtained by placing an earplug conditioned in an environmental room set to 73° F. and 50 percent relative humidity for 48 hours between parallel feet having matching straight edges of 0.8 inches of a Chatillon DGGS Force Gauge (0.1 gm-250 gm) mounted on an LTS stand. The parallel feet were adjusted using a 0.375 inch calibration pin placed between the feet such that spacing between the feet was 0.375 inches and a force reading between 20 to 70 grams was obtained. The force gauge was positioned in a temperature chamber capable of controlling to 96° F.±1° F. After the temperature chamber reached 96° F.±1° F. for 30 minutes, a maximum force measured in 30 second intervals was recorded for 10 minutes. The average of the maximum forces measured in each 30 second interval represented the equilibrium force.

Procedure 2: Fatigue Cycle Test

A leading end of an earplug is adhered in a 9.5 mm diameter and 25 mm deep recess of a fixture using LOCTITE 403 cyanoacrylate adhesive. The fixture was mounted onto a Model 5967 tensile machine available from Instron of Norwood, Mass., and the vertically oriented stem portion was clamped in pneumatic jaws of the tensile machine. The tensile machine was programmed to pull the fixture and pneumatic jaws until a force of 2.5 lbs was achieved and then return to a home position. The home position was maintained for approximately 5 seconds and the tensile machine again pulled to a force of 2.5 lbs. The process was repeated for 200 cycles or until failure.

Examples 1 and 2

Figure 7:
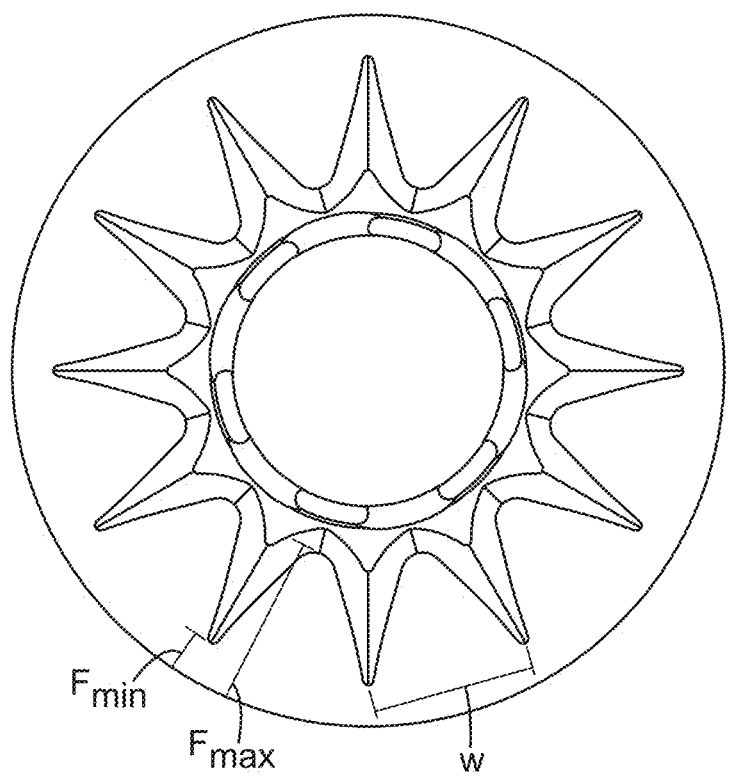
FIGS. 7 and 8 are bottom views of exemplary earplugs according to the present description.
Figure 8:
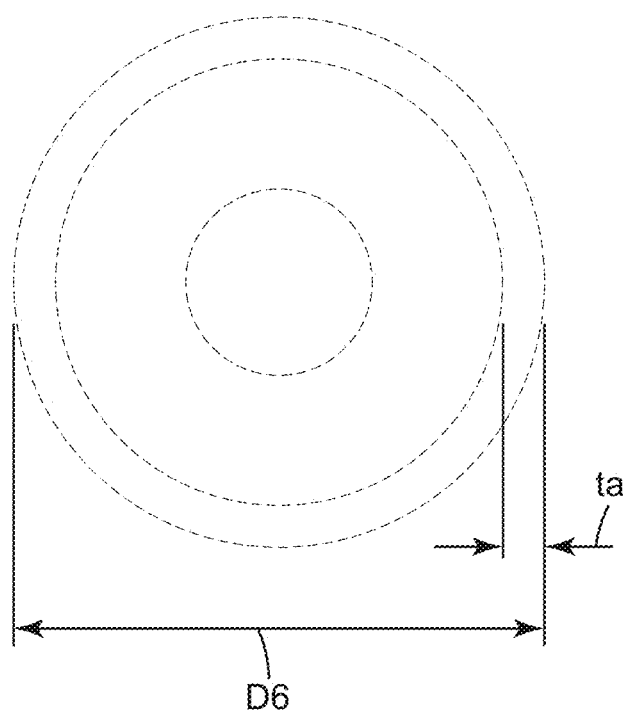

The sample of Examples 1, 2 and Comparative Example A included a core made from PPC1TF2 Pantone 307C (serial #02271318112) from Washington Penn Plastic Co., Inc. of Frankfort, Ky. and a sound attenuating portion and stem outer layer made from Kraton SEBS resins with a hardness of 32 Shore A, from Kraton Polymers LLC, of Houston, Tex., and included expanded spheres and a chemical foaming agent. The core was coated with the material of the sound attenuating portion and stem outer layer and subsequently placed in a mold and heated to form a sound attenuating portion. The earplug of Example 1 included an array of cavities including 8 cavities having trapezoidal cross-sectional shapes uniformly spaced around the longitudinal axis with a shape and configuration shown in FIGS. 6b and 6c. The earplug of Example 2 had a shape and configuration shown in FIGS. 6b and 7 and included an array of cavities including 6 cavities having generally rectangular cross-sectional shapes uniformly spaced around the longitudinal axis. The earplug of Comparative Example A had a shape and configuration shown in FIGS. 6b and 8 but did not include an array of cavities.

The dimensions of the earplugs of Examples 1 and 2 and Comparative Example A are summarized in Table 1. Cavity wall thickness (Tw) was measured at a plane intersecting the array of cavities at a distance (L4) from the leading end.

TABLE 1

|    | Example 1 | Example 2 | Comparative Example A |
|----|-----------|-----------|----------------------|
| L1 | 2.5       | 2.5       | 2.5                  |
| L2 | 4.0       | 4.0       | 4.0                  |
| L3 | 4.7       | 6.4       | —                    |
| L4 | 7.0       | 7.0       | 7.0                  |
| L5 | 8.9       | 8.0       | 8.2                  |
| L6 | 16.5      | 16.5      | 16.5                 |
| L7 | 27.7      | 27.7      | 27.7                 |
| D1 | 2.6       | 2.6       | 2.6                  |
| D2 | 2.6       | 2.6       | 2.6                  |

TABLE 1-continued

|     | Example 1 | Example 2 | Comparative Example A |
|-----|-----------|-----------|----------------------|
| D3  | 4.0       | 4.0       | 4.0                  |
| D4  | 5.9       | 6.3       | 5.7                  |
| D5  | 10.9      | 10.9      | 10.9                 |
| D6  | 18.9      | 16.8      | 16.0                 |
| d   | .5        | 2.4       | —                    |
| Lc  | 4.1       | 1.6       | —                    |
| Tw  | 1.4       | 1.8       | —                    |
| w   | 6.3       | 4.1       | —                    |
| ta  | —         | —         | 1.3                  |
| Fmin | 1.3      | .5        | —                    |
| Fmax | 4.2      | 3.9       | —                    |

Results of the Equilibrium Force Test and Fatigue Cycle Test are reported in Table 2 below. Examples 1 and 2 including an array of cavities having a cavity area (Ac) of 12.3 mm$^2$ and 6.7 mm$^2$, respectively, at a distance L5 from the leading end, showed a 38 percent and 14 percent reduction in equilibrium force as compared to Comparative Example A, while successfully completing the Fatigue Cycle Test. Accordingly, Examples 1 and 2 having an array of cavities reduced the equilibrium force exerted by the earplug and thus are likely to provide a comfortable fit for a user, particularly if worn for an extended period of time. Further, the array of cavities resulted in a reduced equilibrium force while maintaining sufficient durability to pass the Fatigue Cycle Test and not fail after 200 cycles.

TABLE 2

|  | L5 (mm) | Ac (sq. mm.) | Am (sq. mm.) | Ac/Am | Equilibrium Force (g) | Percent Reduction | Fatigue Cycle Test (cycles) |
|---|---|---|---|---|---|---|---|
| Comparative Example A | 8.2 | 0 | 61.4 | 0% | 128 | — | 200 |
| Example 1 | 8.9 | 12.3 | 59.1 | 21% | 90.38 | 38% | 200 |
| Example 2 | 8.0 | 6.7 | 57.0 | 12% | 114.35 | 14% | 200 |

Note:
All dimensions (mm)

What is claimed is:

1. An earplug, comprising:
    a stem;
    a sound attenuating body attached to the stem, the sound attenuating body comprising:
        a leading end,
        a base end,
        a tip region positioned rearward of the leading end,
        a longitudinal axis extending between the leading end and the base end,
        a flange between the tip region and the base end, and
        an exterior flange surface and an interior flange surface having a plurality of inwardly projecting splines extending from the base end and towards the tip region;
    a flange cavity comprising a continuous volume between the flange and the stem around the perimeter of the stem; and
    an array of cavities positioned within the tip region and spaced around the longitudinal axis, the array of cavities comprising a collapsible volume;
    wherein the tip region, at a plane intersecting the array of cavities transverse to the longitudinal axis, comprises a cavity area (Ac), a material area (Am) and an area aspect ratio (Ac/Am), wherein 0.10<(Ac/Am)<0.35.

2. The earplug of claim 1, wherein 0.15<(Ac/Am)<0.30 at a plane intersecting the array of cavities transverse to the longitudinal axis at a distance between 8 mm and 9 mm from the leading end.

3. The earplug of claim 1, wherein 0.10<(Ac/Am)<0.30 at a plane intersecting the array of cavities transverse to the longitudinal axis at a distance between 8 mm and 9 mm from the leading end.

4. The earplug of claim 1, wherein a maximum area aspect ratio (Ac/Am) at a plane intersecting the array of cavities transverse to the longitudinal axis at a distance between 7 mm and 10 mm from the leading end is between 0.15 and 0.35.

5. The earplug of claim 1, wherein at least a portion of the array of cavities are present at a distance 7 mm from the leading end.

6. The earplug of claim 1, wherein 6 mm$^2$<(Ac)<24 mm$^2$.

7. The earplug of claim 1, wherein the tip region comprises an exterior tip region surface and the cavities each comprise an interior cavity surface separated from the exterior tip region surface by a cavity wall thickness (Tw), and 1.0 mm<(Tw)<2.5 mm.

8. The earplug of claim 1, wherein the array of cavities comprise between 4 and 18 discrete cavities.

9. The earplug of claim 1, wherein the array of cavities comprise between 6 and 12 discrete cavities.

10. The earplug of claim 1, wherein the stem comprises a core made of a first material and an outer layer made of a second material.

11. The earplug of claim 1, wherein the sound attenuating body and the stem comprise a foam.

12. The earplug of claim 1, wherein the sound attenuating body comprises styrene-ethylene-butylene-styrene (SEBS).

13. The earplug of claim 1, wherein the plurality of inwardly projecting splines originate at the base end and extend to the tip region.

14. The earplug of claim 1, wherein a flange cavity bottom is formed at the intersection of the stem and the sound attenuating body, and wherein the tip region extends between the leading end and the flange cavity bottom.

15. An earplug, comprising:
    a stem;
    a sound attenuating body attached to the stem, the sound attenuating body comprising
        a leading end,
        a base end,
        a tip region positioned rearward of the leading end, and
        a flange extending at least partially over the stem and comprising an exterior flange surface and an interior flange surface having a plurality of protrusions and a longitudinal axis extending between the leading end and the base end;
    an array of cavities positioned within the tip region and spaced around the longitudinal axis, the array of cavities comprising a collapsible volume; and
    a flange cavity comprising a continuous volume around a perimeter of the stem between the plurality of protrusions and the stem, wherein a flange cavity bottom is formed by the tip region at the intersection of the stem and the sound attenuating body, wherein the tip region extends between the leading end and the flange cavity bottom, wherein the plurality of protrusions extend from the base end and towards the flange cavity bottom;
    wherein the tip region, at a plane intersecting the array of cavities transverse to the longitudinal axis, comprises a cavity area (Ac), a material area (Am) and an area aspect ratio (Ac/Am), wherein 0.10<(Ac/Am)<0.35.

16. The earplug of claim 15, wherein the stem comprises a core made of a first material and an outer layer made of a second material.

17. The earplug of claim 15, wherein the sound attenuating body and the stem comprise a foam.

18. The earplug of claim 15, wherein the sound attenuating body comprises styrene-ethylene-butylene-styrene (SEBS).

19. The earplug of claim 15, wherein the stem extends along the longitudinal axis away from the leading end and past the base end.

20. The earplug of claim 15, wherein the plurality of protrusions originate at the base end and extend to the flange cavity bottom.

* * * * *